United States Patent [19]

Bark

[11] Patent Number: 4,832,054

[45] Date of Patent: May 23, 1989

[54] SEPTUM

[75] Inventor: Jeffrey E. Bark, Racine, Wis.

[73] Assignee: Medical Engineering Corporation, Racine, Wis.

[21] Appl. No.: 882,731

[22] Filed: Jul. 7, 1986

[51] Int. Cl.⁴ .................................................. A61M 25/00
[52] U.S. Cl. .................................. 128/899; 128/764; 604/9; 604/93
[58] Field of Search ................ 128/1 R, 326, 346, 764, 128/769, 899; 604/6–10, 93, 175, 891, 86, 201, 244, 411; 623/8

[56] References Cited

U.S. PATENT DOCUMENTS

| | | | |
|---|---|---|---|
| 3,990,445 | 11/1976 | Lundquist | 604/86 |
| 4,190,040 | 2/1980 | Schulte | 128/1 R |
| 4,557,722 | 12/1985 | Harris | 604/9 |
| 4,560,375 | 12/1985 | Schulte et al. | 604/8 |
| 4,651,717 | 3/1987 | Jakubczak | 128/1 R |
| 4,673,394 | 6/1987 | Fenton, Jr. et al. | 604/175 |
| 4,710,174 | 12/1987 | Moden et al. | 604/175 |

Primary Examiner—Dalton L. Truluck
Assistant Examiner—Denise Whelton
Attorney, Agent, or Firm—S. E. Krieger

[57] ABSTRACT

The septum includes a unit with two fill chamber sections, each having a corresponding needle penetrable seal member for sealing the respective fill chamber sections. The seal members are oppositely disposed and thereby permit access to a corresponding fill chamber section at two different orientations of the septum. Thus, when the septum has flipped over from its original position, one of the fill chamber sections continues to remain accessible for fluid infusion and/or fluid withdrawal. A needle stop portion in the unit which forms a partition between the fill chamber sections prevents a needle that has entered one of the fill chamber sections from passing out of the other fill chamber section. In several embodiments of the invention, the partitioning needle stop section is moveable and in other embodiments of the invention, the partitioning needle stop section is immoveable. Thus there is provision for expanding and contracting the fill chamber sections in some of the embodiments of the invention. In all embodiments of the invention the fill chamber sections are communicable.

17 Claims, 4 Drawing Sheets

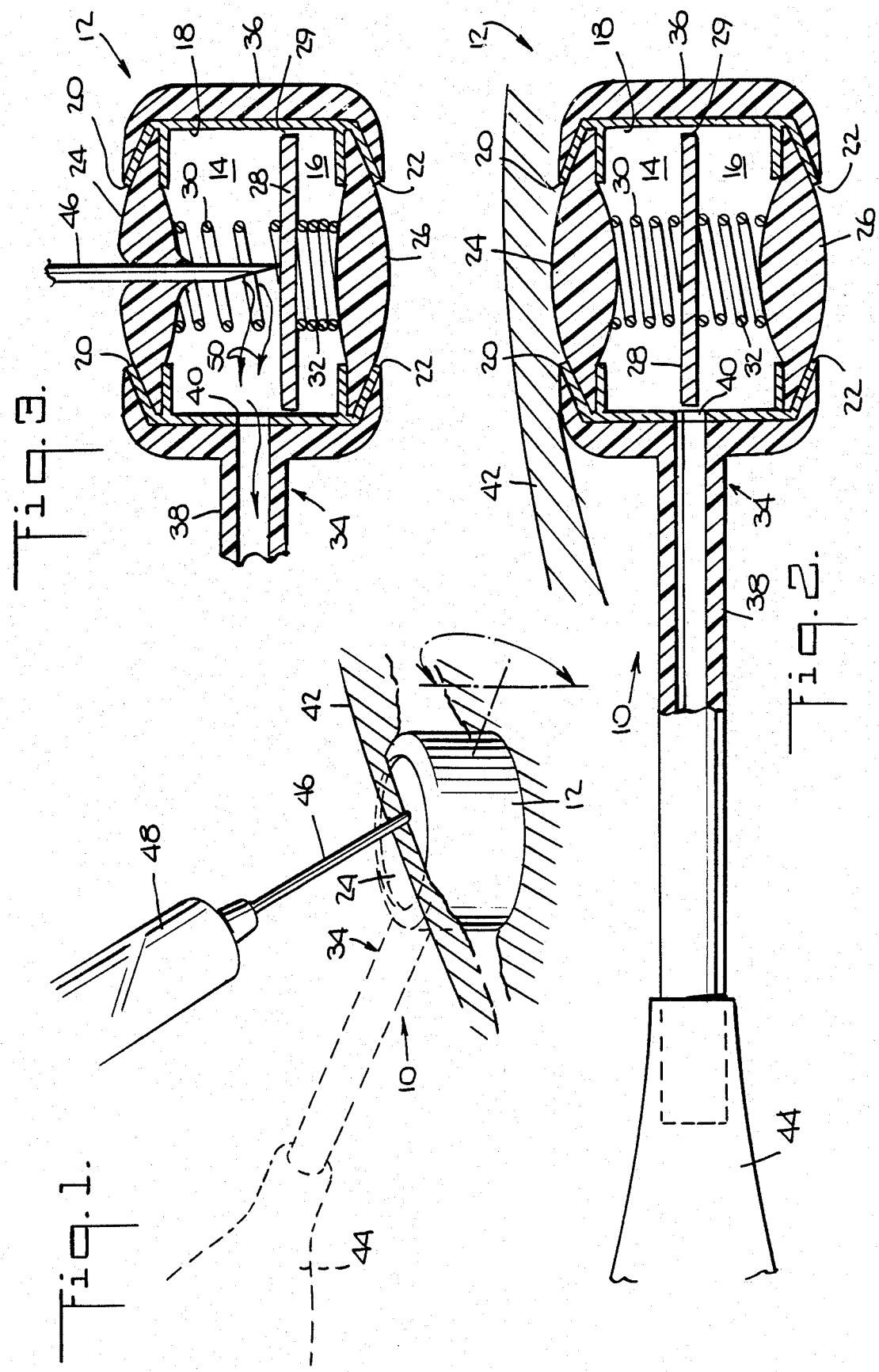

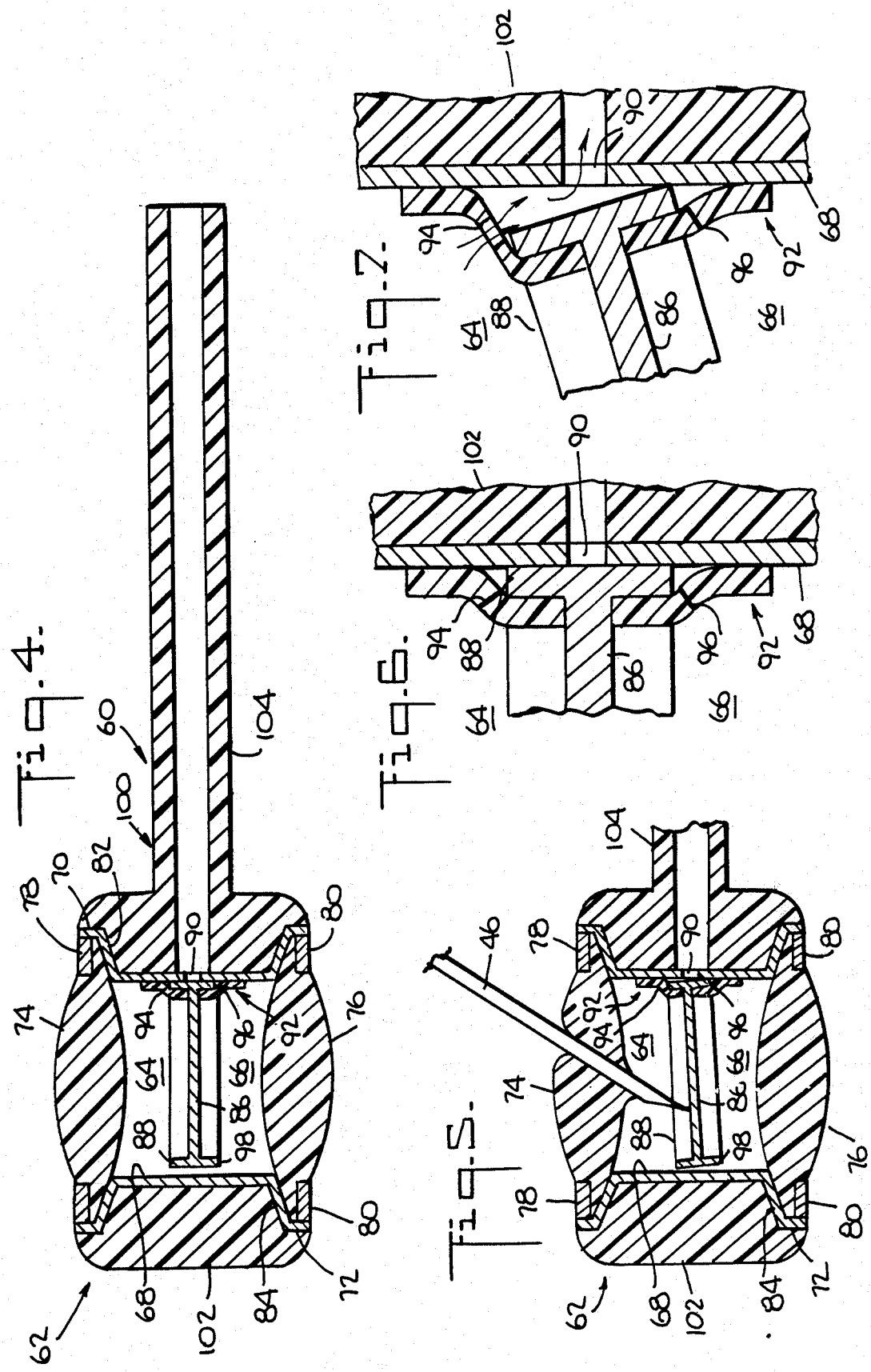

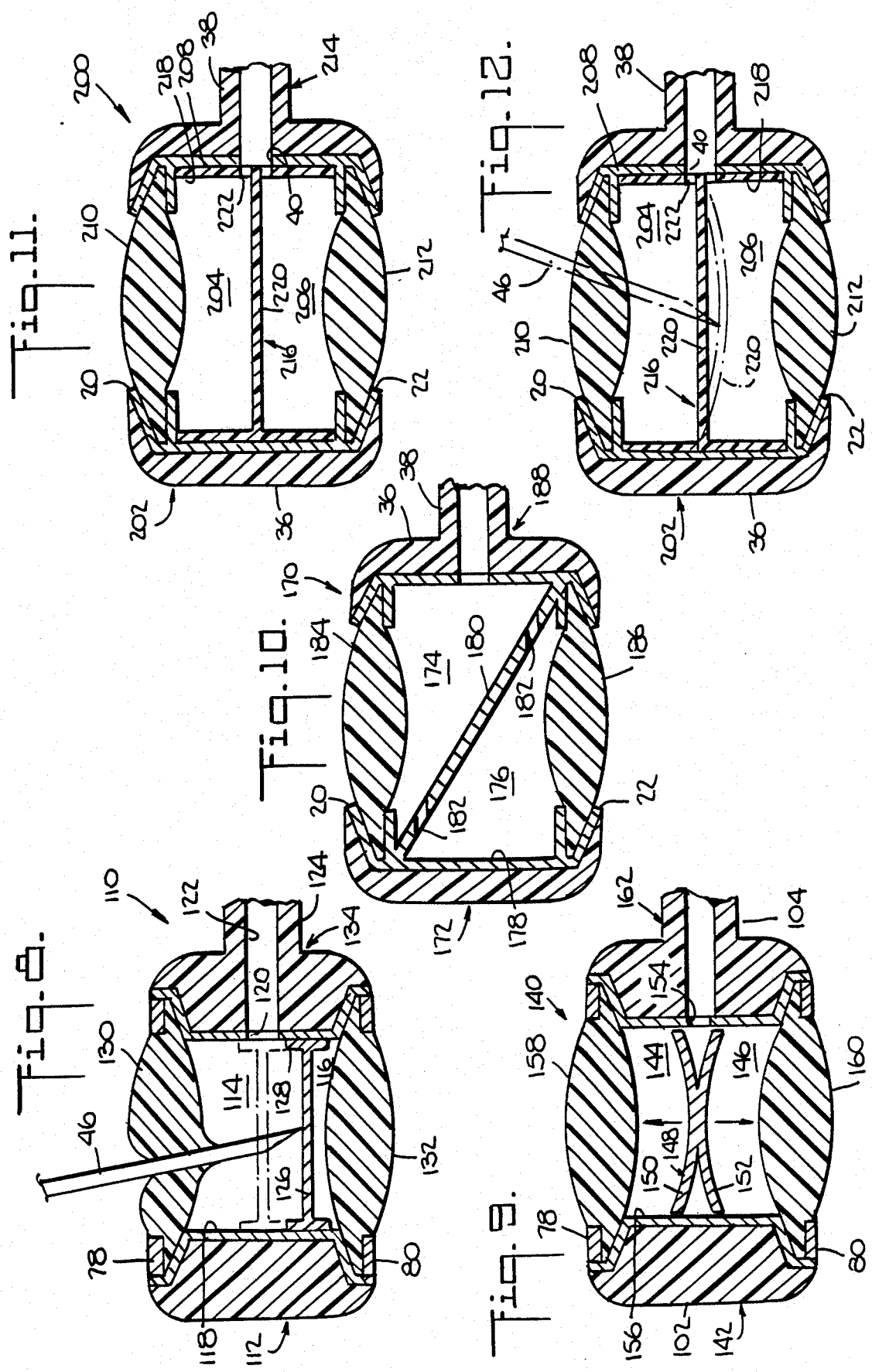

SEPTUM

BACKGROUND OF THE INVENTION

This invention relates to devices for injecting or withdrawing fluids at predetermined regions of the body and more particularly to a novel septum that permits multi-sided access for injection or withdrawal purposes.

Prosthetic devices implanted in the body to restore shapes and contours that have been surgically altered or accidentally deformed usually require infusions of fluid to maintain the desired shape or contour of the prosthesis. The infusions may be required on a periodic basis to vary the volume of fluid within the prosthesis for the purpose of restoring proper pocket tension or modifying the shape or contour of the prosthesis.

Septums are a well know vehicle for directing fluid to a prosthesis and alternatively can be used to drain unwanted fluids from certain areas of the body. A septum, which is generally implanted near a prosthesis, normally includes a fill chamber sealed by a needle penetrable seal member. Fluid is infused into or withdrawn from the fill chamber by a hypodermic needle that accesses the fill chamber through the needle penetrable seal member.

Occasionally a septum will flip over after implantation in a patient. This happens especially in the obese patient where the skin and tissue that surround the septum are somewhat soft and loose. The flipping over of the septum occurs when torsional stresses imposed on the septum by a hypodermic needle, for example, exceed the skin and tissue forces which hold the septum in its desired orientation. Once a septum has lipped over, the fill chamber is no longer easily accessible by a hypodermic needle. Thus, if the flipped over septum is to be of further use it must be repositioned, which may require further surgery.

One approach to improving the stability of a septum is to widen the base of the device. However, increases in the base size of the septum are not always desirable because the necessary surgery to position the septum becomes correspondingly more extensive.

It is thus desirable to provide a septum which remains functional for infusions or withdrawals of fluid even when the septum has flipped over from its original position in the body.

SUMMARY OF THE INVENTION

Among the several objects of the invention may be noted the provision of a novel subcutaneous infusion and withdrawal device, a novel septum that is accessible for fluid infusion and/or fluid withdrawal whether the septum is in an upright or inverted position, a novel septum having dual fill chambers, a novel septum having two separate locations for infusion or drainage of fluids, and a novel method of making a septum.

Other objects and features of the invention will be in part apparent and in part pointed out hereinafter.

In accordance with the present invention, the septum includes a unit with two fill chamber sections, and a pair of oppositely disposed needle penetrable seal members that seal the respective fill chamber sections. A needle stop section is provided between the oppositely disposed needle penetrable seal members to prevent a needle that penetrates one of the needle penetrable seal members from passing though the other needle penetrable seal member. Each of the fill chamber sections communicate with a fluid transfer tube that directs fluid from the septum to a predetermined region of the body such as the site of a prosthesis.

The septum is implanted in the body with one of the two needle penetrable seal members oriented to permit access to a corresponding fill chamber section.

The other needle penetrable seal member and its corresponding fill chamber section are normally not accessible by a hypodermic needle.

However, in the event that the septum flips over, the normally non-accessible needle penetrable seal member and its corresponding fill chamber section become situated in an accessible position whereas the previously accessible needle penetrable seal member and its corresponding fill chamber section become non-accessible.

The septum thus remains functional, despite its flipped over condition, by permitting access to at least one of the needle penetrable seal members and its corresponding fill chamber section.

In the event that the septum flips over more than once, there is generally access to one of the needle penetrable seal members and its corresponding fill chamber section. Thus the septum of the present invention remains functional even when it has undergone a shift in position which renders a previously accessible fill chamber section inaccessible.

In several embodiments of the invention the fill chamber sections are divided by a needle stop section that extends across the fill chamber sections.

In one embodiment of the invention, the needle stop section is moveable relative to the needle penetrable seal members under the influence of a hypodermic needle which can deflect the needle stop section from a normally undeflected position. The moveable needle stop section can be held in position by biasing means or may constitute a freely positioned member.

In a further embodiment of the invention, the needle stop member is in a fixed position between the needle penetrable seal members.

In another embodiment of the invention, the needle stop member is distensable.

In several embodiments of the invention, the fill chamber sections communicate with each other through openings in the needle stop member and/or through a clearance space between the needle stop member and a wall of the fill chamber sections.

In still another embodiment of the invention, the needle stop member pivots to open a normally closed opening to establish communication between one of the fill chamber sections and the fluid transfer tube.

In several embodiments of the invention, a further needle stop section defining a periphery of the fill chamber sections extends from one of the needle penetrable seal members to the other needle penetrable seal member.

In another embodiment of the invention, the fill chamber sections are non-communicable with each other. The needle stop section between the needle penetrable seal members comprises a fixed base or base portions of the respective fill chamber sections. This embodiment can be formed, for example, by providing two single chamber septums joined together back to back. The back portions of the respective septums constitute needle stop means that prevent a needle which penetrates one of the needle penetrable seal members from passing through the other needle penetrable seal member.

In all embodiments of the invention, a single fluid transfer tube can be provided to communicate with both of the fill chamber sections.

The invention accordingly comprises the constructions and method hereinafter described, the scope of the invention being indicated in the claims.

DESCRIPTION OF THE DRAWINGS

In the accompanying drawings, in which several embodiments of the invention are illustrated, FIG. 1 is a perspective view of a septum incorporating one embodiment of the present invention;

FIG. 2 is an enlarged sectional view thereof;

FIG. 3 is an enlarged fragmentary sectional view thereof showing the septum during infusion;

FIG. 4 is an enlarged sectional view of another embodiment of the invention;

FIG. 5 is a fragmentary sectional view showing the septum during infusion by a hypodermic needle;

FIG. 6 is an enlarged fragmentary sectional view of the needle stop pivot arrangement and the fill chamber openings in a closed position;

FIG. 7 is a view similar to FIG. 6 with the needle stop member being pivoted to open one of the fill chamber openings;

FIGS. 8–11 are sectional views of further embodiments of the invention;

FIG. 12 is a view similar to FIG. 11 showing the distensability of the needle stop member under the influence of a hypodermic needle; and, FIG. 13 is a sectional view of another embodiment of the invention.

Corresponding reference characters indicate corresponding parts throughout the several views of the drawings.

DETAILED DESCRIPTION OF THE INVENTION

Figure 13:
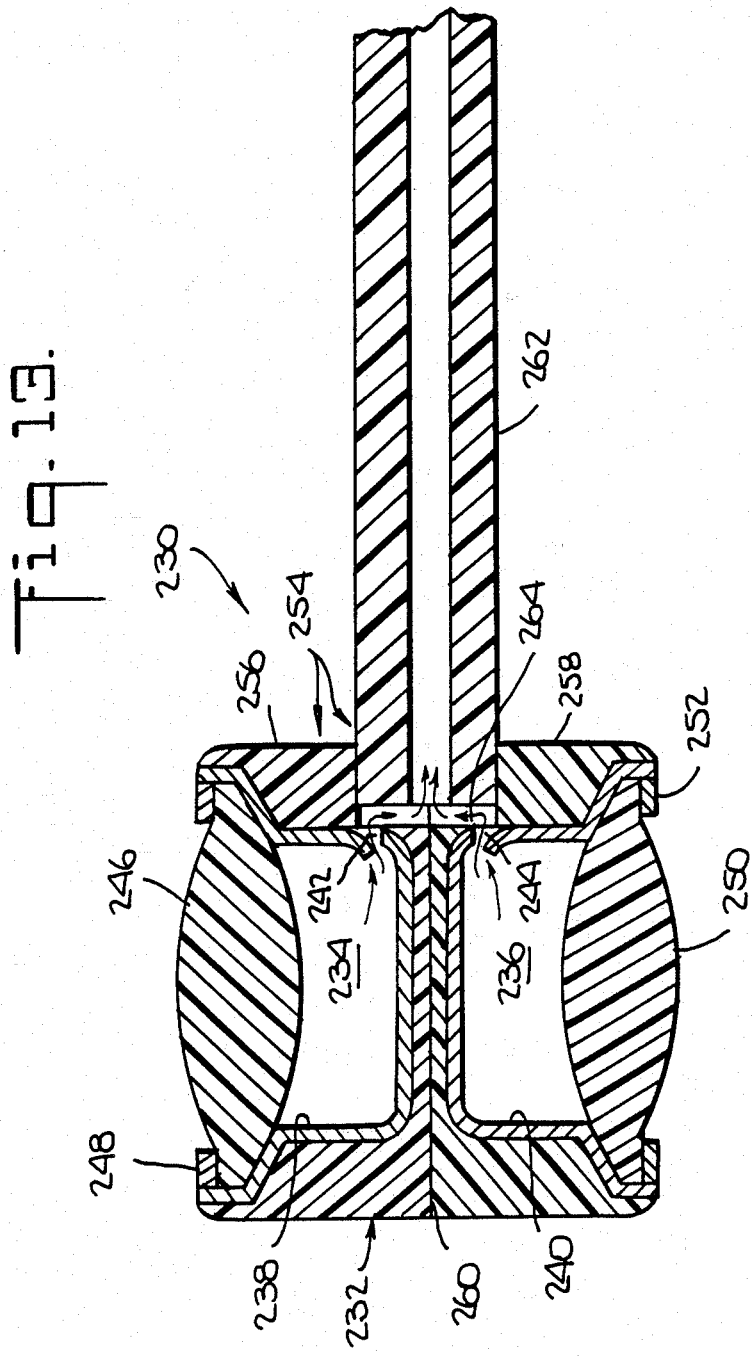

A septum incorporating one embodiment of the invention is generally indicated by the reference number 10 in FIG. 1.

Referring to FIGS. 2 and 3, the septum 10 comprises a hollow unit portion 12 having a pair of fill chamber sections 14 and 16. A generally cylindrical needle stop section 18 defines a perimeter of the fill chamber sections 14 and 16. However, with regard to this and other embodiments of the invention, the cross-sectional shape of the needle stop section 18 as well as the unit 12 is a matter of choice and can be oval or rectangular, for example.

Peripheral channels 20 and 22 formed at opposite ends of the needle stop section 18 accommodate respective needle penetrable seal members 24 and 26 that provide a leak tight seal for the fill chamber sections 14 and 16. Preferably the needle penetrable seal members 24 and 26 are formed of a silicone elastomer. The needle stop section 18 thus extends from the needle penetrable seal member 24 to the needle penetrable seal member 26.

A plate-like needle stop section 28 is provided between the needle penetrable seal members 24 and 26. The needle stop section 28 extends substantially across the fill chamber sections 14 and 16 with a predetermined peripheral clearance 29 from the needle stop section 18. The needle stop section 28 thus constitutes a partition between the fill chamber sections 14 and 16. The needle stop sections 18 and 28 are preferably formed of stainless steel.

Biasing means including a pair of springs 30 and 32 disposed between the needle stop section 28 and the respective needle penetrable seal members 24 and 26 help maintain the needle stop section 28 midway between the needle penetrable seal members 24 and 26. Under this arrangement, the needle stop section 28 is a moveable member capable of shifting its position relative to the needle penetrable seal members 24 and 26.

A jacket 34, preferably made of a silicone elastomer, includes a jacket shell portion 36 formed around the exterior of the needle stop section 18. The jacket 34 also includes an integral fluid transfer tube 38 that extends away from the jacket shell 36 in communication with the fill chamber sections 14 and 16 through an opening 40 in the needle stop section 18.

In using the septum 10, an implantation thereof is made under the skin 42 with the fluid transfer tube 38 directed toward a prosthesis 44, for example. Before the implanted septum 10 can be infused, it is usually located by palpating the skin 42 covering the area of the septum 10. With the septum 10 positioned as shown in FIG. 2, the needle penetrable seal member 24 is accessible to a needle 46 of a syringe 48 which contains a desired fluid supply.

As shown in FIG. 3, the needle 46 upon penetration of the seal member 24 communicates with the fill chamber section 14. The needle 46 upon entering the fill chamber section 14 will usually engage the needle stop section 28, and upon so doing, will deflect the needle stop section 28 toward the needle penetrable seal member 26. The needle 46 can thus cause the volume of the fill chamber section 14 to expand thereby decreasing the volume of the fill chamber section 16. Thus the fill chamber sections 14 and 16 are portions of a single space within the unit 12, the chamber sections 14 and 16 being variable in size depending upon the position of the needle stop member 28.

Fluid from the needle 46, represented by the arrows 50 in FIG. 3, fills the chamber section 14 and can also flow into the chamber section 16 through the clearance space 29 provided between the needle stop section 28 and the needle stop section 18. Openings (not shown) can also be provided in the needle stop section 28 to enhance communication between the fill chamber sections 14 and 16.

The fluid 50 flows outwardly of the fill chamber section 14 through the opening 40 of the needle stop section 18 and into the fluid transfer tube 38 which directs such fluid toward the prosthesis 44.

The septum 10, is initially oriented with the needle penetrable seal member 24 and the fill chamber 14 in a position accessible to the hypodermic needle 46. This orientation can change if the septum 10 flips over due to torsional stresses imposed on the device 10 that overcome the holding forces normally present during implantation.

Should the septum 10 flip over, the needle penetrable seal member 26 and its corresponding fill chamber section 16 will become accessible to the needle 46. The previously accessible needle penetrable seal member 24 and its corresponding fill chamber section 14, following a septum flip over, will become inaccessible to the needle 46. Nevertheless the septum 10 continues to function as an infusion device since one of the two fill chamber sections 14 and 16 are accessible by the needle 46 through one of the two needle penetrable seal members 24 or 26.

Another embodiment of the septum is generally indicated by the reference number 60 in FIG. 4. The septum 60 comprises a hollow unit portion 62 having a pair of fill chamber sections 64 and 66. A generally cylindrical needle stop section 68 defines a perimeter of the fill chamber sections 64 and 66.

Peripheral lip portions 70 and 72 formed at opposite ends of the needle stop section 68 accommodate respective needle penetrable seal members 74 and 76. Clamping rings 78 and 80 are threaded, staked, press-fit or otherwise joined to the respective lip portions 70 and 72. The clamping rings 78 and 80 are arranged to press the peripheral portions of the needle penetrable seal members 74 and 76 against the respective lip flanges 82 and 84 to provide a leak-tight seal for the fill chamber sections 64 and 66. The needle stop section 68 thus extends from the needle penetrable seal member 74 to the needle penetrable seal member 76.

A plate-like needle stop section 86 having an annular collar 88 is provided between the needle penetrable seal members 74 and 76. A portion of the collar 88 is secured against an opening 90 in the needle stop section 68 by an elastic hinge 92, preferably formed of silicone elastomer. The shape of the hinge 92 can be circular, elliptical or rectangular, for example.

The hinge 92 includes one or more normally closed exit ports 94 (FIGS. 6 and 7) within the fill chamber section 64, and one or more normally closed exit ports 96 within the fill chamber section 66. The needle stop section 86 extends substantially across the fill chamber sections 64 and 66 with a predetermined peripheral clearance 98 from the needle stop section 68. The needle stop section 86 is thus pivoted to the needle stop section 68 at the hinge 92.

A jacket 100, similar to the jacket 34 of the septum 10, includes a jacket shell portion 102 formed around the needle stop section 68. The jacket 100 also includes an integrally formed fluid transfer tube 104 that extends away from the jacket shell 102 in communication with the opening 90 of the needle stop section 68. When the exit port 94 in the fill chamber section 64 is normally closed there is no communication between the fill chamber section 64, for example, and the fluid transfer tube 104.

In using the septum 60 for infusion purposes, the needle penetrable seal member 74 is penetrated by a needle 46 as shown in FIG. 5. A bottoming of the needle 46 against the needle stop section 86 causes the needle stop section 86 to pivot toward the needle penetrable seal member 76.

Referring to FIGS. 6 and 7, pivotal movement of the needle stop section 86 elongates the hinge 92 in the area of the exit port 94 thereby causing the exit port 94 to open. Communication is thus established between the fill chamber section 64 and the fluid transfer tube 104 through the opening 90 in the needle stop section 68.

In the event that the septum 60 flips over from the orientation shown in FIGS. 4–7, the needle penetrable seal member 76 and its corresponding fill chamber section 66 will become accessible to the needle 46. Accordingly, penetration of the needle 46 into the fill chamber section 66 will pivot the needle stop section 86 in a direction opposite that shown in FIG. 7 thereby causing the exit port 96 to open and permit communication between the fill chamber section 66 and the fluid transfer tube 104.

The hinge 92 thus functions as a valve which opens and closes the exit ports 94 and 96 upon movement of the needle stop section 86 in a predetermined direction by the needle 46.

A further embodiment of the septum is generally indicated by the reference number 110 in FIG. 8. The septum 110 comprises a hollow unit portion 112 having a pair of fill chamber sections 114 and 116. A generally cylindrical needle stop section 118 forms a border of the fill chamber sections 114 and 116.

The needle stop section 118 includes an opening 120 that is substantially equivalent in size to the fluid passage 122 nn a fluid transfer tube 124. The septum 110 also includes a plate-like needle stop section 126 having an annular collar 128 similar to the needle stop section 86 of the septum 60.

The needle stop section 126, by virtue of a predetermined clearance between the collar 128 and the needle stop section 118, is freely moveable within the fill chamber sections 114 and 116. The fill chamber sections 114 and 116 are thus communicable through the clearance around the needle stop section 126.

The septum 110 also includes oppositely disposed needle penetrable seal members 130 and 132 identical to the seal members 74 an 76 of the septum 60. The seal members 130 and 132 are retained in the needle stop section 118 in an arrangement similar to that described for the septum 60. A jacket 134 surrounding the needle stop section 118 is identical to the jacket 34 of the septum 60.

The septum 110 is used in a manner similar to that previously described for the septum 60. However the needle 46, after penetrating the seal member 130 and engaging the needle stop section 126, will urge the needle stop section 126 toward the seal member 132. Consequently the fill chamber section 114 will expand while the fill chamber section 116 is contracted.

Still another embodiment of the septum is generally indicated by the reference number 140 in FIG. 9. The septum 140 comprises a hollow unit portion 142 having a pair of fill chamber sections 144 and 146 partitioned by a plate- like needle stop section 148. The needle stop section 148 includes two dished portions 150 and 152 joined to define an annular space 154 therebetween.

A generally cylindrical needle stop section 156, identical to the needle stop section 118 of the septum 110, forms a border of the fill chamber sections 144 and 146. The needle stop section 148 is freely movable by a syringe needle (not shown) within the fill chamber sections 144 and 146 due to a predetermined clearance from the needle stop section 156.

The septum 140 further includes needle penetrable seal members 158 and 160 identical to the seal members 74 and 76 of the septum 60. The seal members 158 and 160 are retained in the needle stop section 156 in an arrangement similar to that of the septum 60. The septum 140 also includes a jacket 162 identical to the jacket 100 of the septum 60. The septum 140 is used in a manner similar to that described for the septum 110.

Another embodiment of the septum is generally indicated by the reference number 170 in FIG. 10. The septum 170 comprises a hollow unit portion 172 having a pair of fill chambers 174 and 176. A generally cylindrical needle stop section 178 forms a border of the fill chamber sections 174 and 176.

A plate-like needle stop section 180, diagonally disposed in the needle stop section 178, forms a fixed partition between the fill chamber sections 174 and 176. Apertures 182 formed in the needle stop section 180 permit communication between the fill chamber sections 174 and 176. The apertures 182 are formed at a predetermined angle to the plane of the needle stop section 180 such that a needle (not shown) which passes into one fill chamber section and engages the needle stop section 180 cannot pass through the apertures 182 and out of the opposite fill chamber section.

The septum 170 further includes needle penetrable seal members 184 and 186, identical to the seal members 24 and 26 of the septum 10. The seal members 184 and 186 are retained in the needle stop section 178 in an arrangement similar to that of the septum 10. The septum 170 also includes a jacket 188 identical to the jacket 34 of the septum 10.

The septum 170 is used nn a manner similar to that described for the septum 10. However, engagement of the needle stop section 180 by a needle (not shown) does not displace the needle stop section 180. Therefore the fill chamber sections 174 and 176 are not expandable or contractable.

An additional embodiment of the invention is generally indicated by the reference number 200 in FIG. 11. The septum 200 comprises a hollow unit portion 202 having a pair of fill chamber sections 204 and 206. The septum 200 also includes a generally cylindrical nondeflectable needle stop section 208, needle penetrable seal members 210 and 212 and a jacket 214 respectively identical to the needle stop section 18, the seal members 24, 26 and the jacket 34 of the septum 10.

A deflectable needle stop section 216 is disposed within the nondeflectable needle top section 208. The deflectable needle stop section 216 includes a generally cylindrical portion 218 preferably formed of a silicone elastomer bonded or otherwise secured to the nondeflectable needle stop section 208, and deflectable, porous, plate-like needle stop portion 220 preferably formed of stainless steel mesh.

The deflectable needle stop portion 220, which is integrally joined to the cylindrical portion 218, forms a partition between the fill chamber sections 204 and 206. The fill chamber sections 204 and 206 are communicable through the pores of the deflectable needle stop portion 220. An annular opening 222 formed in the cylindrical portion 218 aligns with the opening 40 of the needle stop section 208.

The septum 200 is used in a manner similar to that previously described for the septum 10. However, when a needle 46 engages the deflectable needle stop portion 220, as shown in FIG. 12, a deflection of such needle stop section occurs resulting in an expansion of the fill chamber section 204 and a corresponding contraction of the fill chamber section 206. Although the deflectable needle stop portion 220 is porous it does not permit penetration of the needle 46. Fluid injected into the fill chamber section 204 by the needle 46 will flow through the annular opening 222 into the fluid transfer tube 38.

Another embodiment of the invention is generally indicated by the reference number 230 in FIG. 13. The septum 230 comprises a unit portion 232 having a pair of fill chamber sections 234 and 236. Each of the fill chambers 234 and 236 is bordered by respective cup-shaped needle stop sections 238 and 240. The needle stop sections 238 and 240 include respective fluid transfer openings 242 and 244.

A needle penetrable seal member 246 is retained in the needle stop section 238 by a clamping ring 248 in an arrangement identical to that of the septum 60. A needle penetrable seal member 250 is similarly retained in the needle stop section 240 by a clamping ring 252.

The septum 230 also includes a jacket 254 comprising jacket shells 256 and 258 adhered or otherwise bonded together at a seam line 260. The jacket 254 also includes a fluid transfer tube 262 joined to the shell portions 256 and 258. The fluid transfer tube 262 aligns with the needle stop fluid transfer openings 242 and 244. A communication space 264 is provided between the fluid transfer tube 262 and the needle stop fluid transfer openings 242 and 244 to permit both fill chamber sections 234 and 236 to communicate with the fluid transfer tube 262. The communication space 264 also permits communication between the fill chamber sections 234 and 236.

The septum 230 is used in a manner similar to that described for the septum 10. However the fill chamber sections 234 and 236 are not expandable or contractable.

Some advantages of the present invention evident from the foregoing description include a septum that is accessible at two different orientations for fluid infusion or fluid withdrawal. Consequently, the potential flipping over of the septum from its original position in the body does not represent a problem requiring surgical intervention. The dual accessibility of the fill chambers enables the septum to remain functional even after a flipped over condition has occurred. A further advantage is the prolongation of the useful life of the septum, since it continues to be usable under circumstances where a single-sided septum has become unusable.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A septum comprising, a unit with a pair of opposing needle penetrable seal members, a chamber within said unit for receiving fluid, needle stop means provided between said needle penetrable seal members for preventing a needle that penetrates one of said needle penetrable seal member from passing though the other said needle penetrable seal member, said needle stop means including a first needle stop section that extends substantially across said one chamber and divides said one chamber into two fill chamber section, and means for permitting communication between said fill chamber sections.

2. The septum as claimed in claim 1, wherein said communication means includes openings in said needle stop section.

3. The septum as claimed in claim 1, wherein said communication means include a predetermined clearance between said needle stop section and said fill chamber sections.

4. The septum as claimed in claim 1, including a communication space outside said two chambers for permitting communication between said two chambers.

5. The septum as claimed in claim 1, wherein said needle stop means are immovable.

6. The septum as claimed in claim 1, wherein said needle stop section is in a fixed position in said unit.

7. The septum as claimed in claim 1, wherein said needle stop section is deflectable.

8. The septum as claimed in claim 1, wherein said needle stop section is movable in said chamber such that said movement causes expansion of one of said fill chamber sections and contraction of the other said fill chamber section.

9. The septum as claimed in claim 8, wherein biasing means are provided between said needle stop section and each of said needle penetrable seal members to maintain said needle stop section in a predetermined position when said needle stop section is not being deflected.

10. The septum as claimed in claim 8, wherein said fill chamber sections include a wall and said needle stop section includes means for pivoting said needle stop section to said wall for pivotal movement in response to deflection by a needle.

11. The septum as claimed in claim 10, wherein said needle stop section has a normally undeflected position and said pivot means includes at least one fluid flow opening that is normally closed when said needle stop section is in said undeflected position, said one fluid flow opening being rendered open when said needle stop section is deflected in a predetermined direction.

12. The septum as claimed in claim 1, wherein said needle stop means includes a second needle stop section defining a perimeter of said dual fill chamber sections and extending from one of said needle penetrable seal members toward the other said needle penetrable seal member, and said septum further includes flow means communicable with each of said dual fill chamber sections extending outwardly of said dual fill chamber sections.

13. A septum comprising, an implantable unit with two fill chamber sections, a pair of needle penetrable seal means for sealing the respective fill chamber sections, an needle stop means provided between said needle penetrable seal means for preventing a needle that penetrates one of said needle penetrable seal means from passing through the other said needle penetrable seal means, said needle stop means including a movable needle stop section.

14. The septum as claimed in claim 13, wherein said needle stop means is immovable.

15. The septum as claimed in claim 13, wherein said needle stop means include means for permitting communication between said fill chamber sections.

16. The septum as claimed in claim 13, including a communication space outside said fill chamber sections for permitting communication between said fill chamber sections.

17. A method of making a septum comprising,
(a) forming an implantable unit with a pair of fill chamber sections that are divided by a needle stop section,
(b) sealing the fill chamber sections with respective opposing needle penetrable seal members.
(c) establishing communication between each of said fill chamber sections, and
(d) providing fluid flow means for directing flow of fluid away from and/or toward said fill chamber sections.

* * * * *